United States Patent [19]

Iwataki et al.

[11] Patent Number: 4,482,740
[45] Date of Patent: Nov. 13, 1984

[54] 5-PHENYLCYCLOHEXENONE DERIVATIVES

[75] Inventors: Isao Iwataki; Akira Nakayama; Minoru Kaeriyama; Hisao Ishikawa; Hideo Hosaka; Kenichi Kohara; Shozo Yamada, all of Kanagawa, Japan

[73] Assignee: Nippon Soda Company Limited, Tokyo, Japan

[21] Appl. No.: 453,499

[22] Filed: Dec. 27, 1982

[30] Foreign Application Priority Data

Dec. 29, 1981 [JP] Japan .................................. 56-210452

[51] Int. Cl.³ ........................ C07C 143/75; C07F 1/08
[52] U.S. Cl. .................................. 564/99; 260/438.1; 260/429 R; 260/429.9; 260/430; 260/439 R; 71/88
[58] Field of Search .................. 564/99; 71/88; 260/429 R, 438.1, 429.9, 439 R, 430

[56] References Cited

U.S. PATENT DOCUMENTS

| | | | |
|---|---|---|---|
| 3,875,149 | 4/1975 | Woolridge et al. | 564/99 X |
| 3,950,420 | 4/1976 | Sawaki et al. | 71/88 X |
| 4,052,194 | 10/1977 | Wilcox | 71/88 X |
| 4,117,154 | 9/1978 | Stetter et al. | 564/99 X |
| 4,174,210 | 11/1979 | Schinski et al. | 71/88 X |
| 4,269,775 | 5/1981 | Szczepanski et al. | 71/88 X |
| 4,294,772 | 10/1981 | Martin | 71/88 X |
| 4,347,372 | 8/1982 | Föry et al. | 71/88 X |

Primary Examiner—Helen M. S. Sneed
Attorney, Agent, or Firm—George B. Oujevolk

[57] ABSTRACT

A compound having the general formula

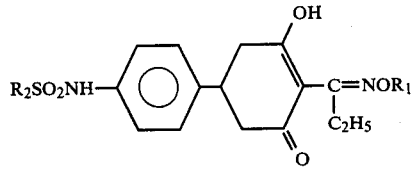

wherein
  $R_1$ is ethyl or allyl; and
  $R_2$ is alkyl having 1-4 carbon atoms;
and a metal salt of the compound defined herein above.
The compound is useful as herbicides.

1 Claim, No Drawings

5-PHENYLCYCLOHEXENONE DERIVATIVES

The present invention relates to cyclohexenone derivatives, to a process for the preparation thereof and their uses as selective herbicides.

According to the present invention, there are provided a compound of the formula

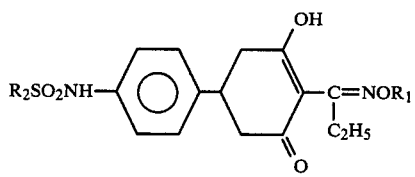

wherein
$R_1$ is ethyl or allyl; and
$R_2$ is alkyl having 1-4 carbon atoms;
and a metal salt of the compound defined herein above.

It is disclosed in U.S. Pat. Nos. 3,950,420 and 4,011,256 some 5-phenyl-cyclohexenone derivatives are useful as herbicides. However, the compounds of this invention containing phenyl substituted with alkylsulfonamide group show much better selectivity against corn, wheat, barley and rice than the known compounds which have phenyl or phenyl substituted with methoxy group, though their herbicidal activities against grass weeds are almost equal.

That is, the known compounds can not be used in cereals such as corn and wheat because of its non-selectivity between gramineous crops and grass weeds, though they are very useful to control grass weeds in broad-leaved crops such as soybean, cucumber and radish. However, compounds of the present invention show only a slightly weak action exceptionally against cereals such as corn, wheat and barley, and a high herbicidal activity on gramineous weeds, especially wild oat. Thus said compounds have quite a unique characteristics compared with the known compounds. They are acceptable to use in both pre- and post-emergence treatment, preferably in post-emergency treatment.

The compounds of this invention can be prepared in accordance with the following equation:

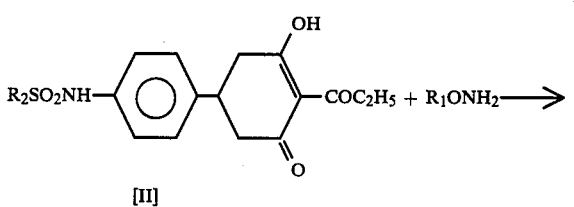

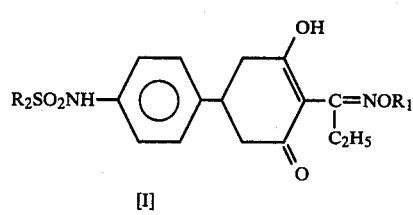

wherein $R_1$ and $R_2$ are as previously defined.

The above reaction can be conducted in an inert solvent.

As an inert solvent, methanol, ethanol, diethyl ether, benzene, toluene, chloroform or the like may be used.

The reaction temperature may be from a room temperature to the boiling point of the reaction solution, preferably at the room temperature or under a miled heating condition, and the reaction may be carried out for half an hour to several hours or longer.

After the reaction has been completed, the solvent is, if necessary, removed and the reaction mixture is then extracted with an alkaline solution. The solution is acidified with hydrochloric acid and the crude product is isolated from the acid mixture by extraction or by filtration.

The crude product can be purified by recrystallization and a chemical formula for the resulting purified compound can be assigned by means of an elemental analysis, NMR spectrum, Mass spectrum and IR spectrum.

The sodium and potassium salts may be prepared by treating a compound of formula [I] with sodium or potassium hydroxide in aqueous solution or in an organic solvent such as acetone, methanol, ethanol or dimethylformamide. The salts may be isolated by filtration or by evaporation of resulting solution.

The calcium, barium, manganese, copper, zinc, nickel, cobalt, iron and silver salts may be prepared from the sodium or potassium salt by treatment with the appropriate inorganic metal salt, e.g. calcium chloride, barium chloride, copper sulfate, zinc chloride, nickel chloride and cobalt nitrate.

The calcium salt may also be prepared by treating a compound of the formula [I] with calcium hydroxide.

Some metal salts produced by above-mentioned process may undergo a chemical change or decomposition at a high temperature, and therefore not show a clear melting point. By applying infrared absorption spectroscopy to the starting material and reaction product, the formation of the metal salt is evidenced by transference of absorption bands and a change of absorption intensity. Thus, the starting material having the formula [I] has the absorption due to the carbonyl group at wavelengths 1605 cm$^{-1}$ and 1655 cm$^{-1}$, whereas the corresponding metal salt shows the absorption at longer wavelengths.

Further, an anion such as OH may be simultaneously coordinated with a metal atom of some metal salts mentioned above.

The structure of the metal salt may be shown as follows:

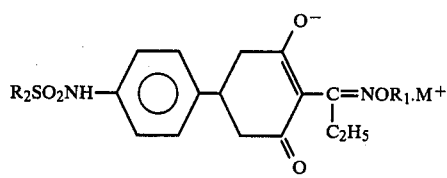

wherein M$^+$ is metal ion such as Na$^+$, $\frac{1}{2}$Ca$^{2+}$ or $\frac{1}{2}$Cu$^{2+}$.

It is expected that the compounds represented by the formula [I] exist in the following tautomeric forms:

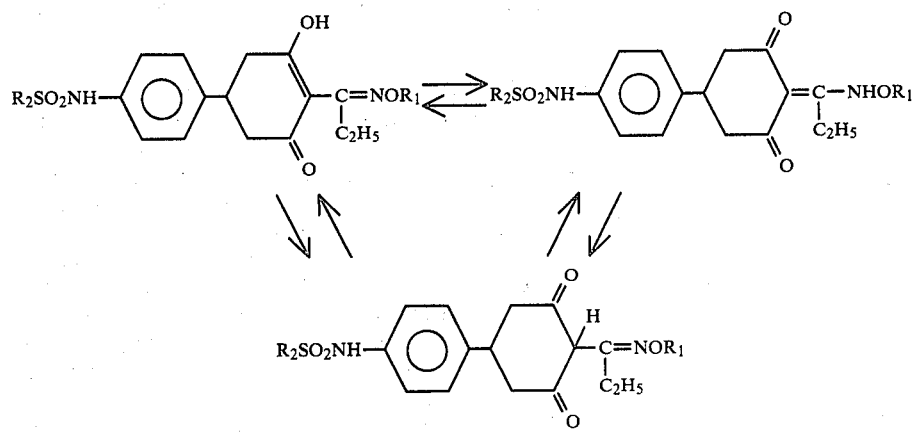

The starting material of the formula [II] can be prepared in accordance with the following equation:

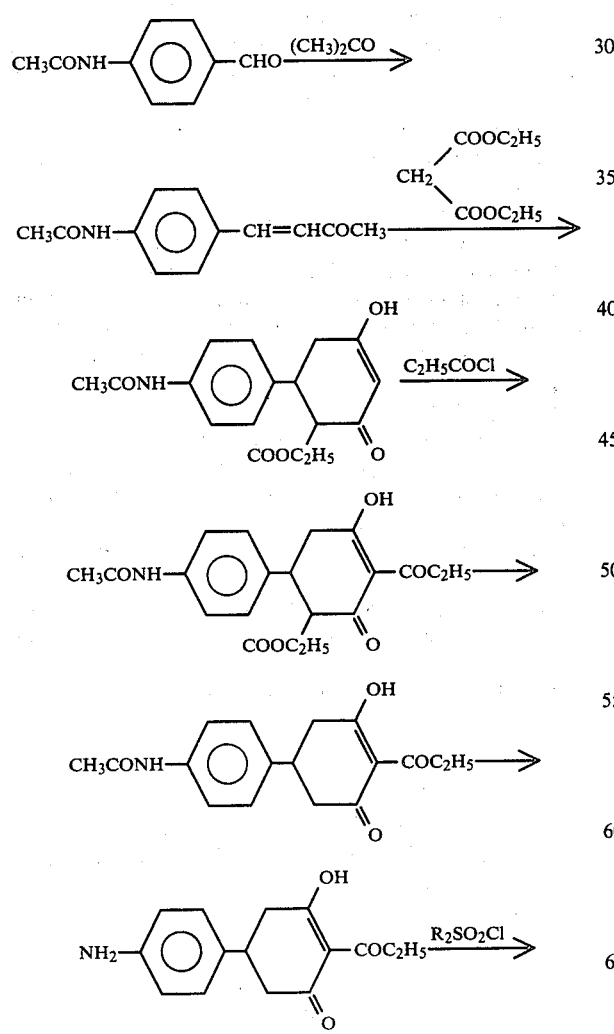

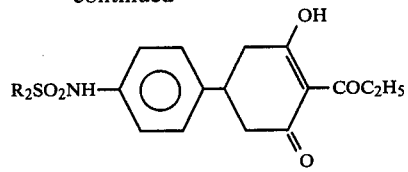

The following Examples illustrate the invention:

EXAMPLE 1

2-[1-(ethoxyimino)propyl]-3-hydroxy-5-(4-methanesulfonamidophenyl)-2-cyclohexen-1one:

Into 10 ml of tetrahydrofuran was dissolved 1.5 g of 3-hydroxy-5-(4-methanesulfonamidophenyl)-2-propionyl-2-cyclohexen-1-one and to the solution was added 0.5 g of ethoxyamine. The mixture was kept at room temperature for 15 hours and poured into ice water. And then the mixture was acidified with hydrochloric acid and it was extracted with chloroform. The chloroform solution was washed with water and extracted with 15 ml of an aqueous solution cotaining 5% of sodium hydroxide. The solution was acidified with hydrochloric acid and the crystal sedimented was extracted with chloroform and the solution was washed with water and it was dried with magnesium sulfate. Then, it was distilled off under a reduced pressure and thus, 1.4 g of the objective compound was obtained. It was colorless crystals having a melting point of 115°–116° C.

EXAMPLE 2

2-[1-(allyloxyimino)propyl]-5-(4-methanesulfonamidophenyl)-3-hydroxy-2-cyclohexen-1-one:

Into 10 ml of tetrahydrofuran was dissolved 1.0 g of 5-(4-methanesulfonamidophenyl)-3-hydroxy-2-propionyl-2-cyclohexen-1-one and to the solution was added 0.5 g of allyloxyamine. The mixture was kept at room temperature for 15 hours and then it was treated with similar process in Example 1. Thus, 0.8 g of the objective compound was obtained. It was colorless crystals having a melting point of 134°–135° C.

EXAMPLE 3

Sodium 2-[1-(ethoxyimino)propyl]-5-(4-methanesulfonamidophenyl)-3-oxo-1-cyclohexenolate:

Into 10 ml of methanol was dissolved 1.9 g of 2-[1-ethoxyimino)propyl]-5-(4-methanesulfonamidophenyl)-3-hydroxy-2-cyclohexen-1-one and to the methanol solution was added 20 ml of methanol containing 0.27 g of sodium methoxide. Then, the solvent was removed under a reduced pressure and the residue was recrystallized with acetonitrile. Thus, 1.8 g of the objective compound which was colorless crystals having a decomposition point of 165°–170° C. was obtained.

EXAMPLE 4

Calcium 2-[1-(ethoxyimino)propyl]-5-(4-methanesulfonamidophenyl)-3-oxo-1-cyclohexenolate:

Into 20 ml of an aqueous solution containing 2% of sodium hydroxide was dissolved 1.9 g of 2-[1-(ethoxyimino)propyl]-5-(4-methanesulfonamidophenyl)-3-hydroxy-2-cyclohexen-1-one and to the solution was added 3 cc of an aqueous solution containing 10% of calcium chloride at room temperature. The water was removed under reduced pressure and the residue was dissolved in ethanol and an insoluble sodium chloride was separated with a filtering step. The ethanol was distilled off under reduced pressure and 1.5 g of white powder having a melting point of 250° C. or more was obtained.

In addition to the above-mentioned compounds, some typical compounds are listed in Table 1.

TABLE 1

$R_2SO_2NH-\text{(phenyl)}-\text{(cyclohexenone)}-C(=NOR_1)-C_2H_5$ with OH

| Compound No. | $R_1$ | $R_2$ | Metal Salt | Physical Constant [ ]° C. |
|---|---|---|---|---|
| 1 | —$C_2H_5$ | —$CH_3$ | — | [115–116] |
| 2 | —$CH_2CH=CH_2$ | —$CH_3$ | — | [134–135] |
| 3 | —$C_2H_5$ | —$C_2H_5$ | — | [119–120] |
| 4 | —$C_2H_5$ | —$nC_3H_7$ | — | [111–112] |
| 5 | —$C_2H_5$ | —$nC_4H_9$ | — | [118–119] |
| 6 | —$C_2H_5$ | —$CH_3$ | Na salt | [165–170] dec. |
| 7 | —$C_2H_5$ | —$CH_3$ | Ca salt | [250° C. up] |

As mentioned previously, the compounds possess superior herbicidal activity. The compounds may be applied directly to the soil as pre-emergence treatment or to plant foliage as post-emergence treatment, or they can be mixed intimately with soil. The preferred treatment is post-emergence treatment and the compounds may be applied to soil or to plant foliage in amount of 5 g or more per 10 are.

A herbicidal composition having a compound of this invention as its active ingredient may be formulated by mixing suitable carriers in a form generally used in agricultural chemicals, such as wettable powder, water soluble powder, emulsifiable concentrate and flowable. As solid carriers, talc, white carbon, bentonite, clay, diatomaceous earth or the like may be used. As liquid carriers, water, alcohol, benzene, xylene, kerosene, mineral oil, cyclohexane, cyclohexanone, dimethylformamide or the like may be used. A surface active agent may, if necessary, be added in order to give a homogeneous and stable formulation.

Compounds can also be applied admixed with other chemicals, which are used in agronomic and horticultural management and which are compatible with such compounds. Such chemicals can be, but are not restricted to, the classes of chemical commonly known as fungicides, insecticides, acaricides, herbicides and plant growth regulators. In particular, by mixing it with the other herbicides, its using chemical amount and manpower can be decreased and furthermore, the higher effect of synergetic function with both chemicals can be expected.

For admixture of the compound with known herbicides, the use is recommended of triazine derivatives such as simazine, atrazine and terbutryne, urea derivatives such as ipuron and tribunyl, heterocyclic compounds such as bentazone, phenoxyalkane carboxilic acid derivatives such as 2,4-D and MCPP, benzonirile derivatives such as ioxynil, and sulfonamide derivatives such as chlorosulfuron.

The concentration of the active ingredient in a herbicidal composition may vary according to type of formulation, and the concentration is, for example, in the range of 5–80 weight percent, preferably 30–60 weight percent, in wettable powder; 70–95 weight percent, preferably 80–90 weight percent, in water soluble powder; 5–70 weight percent, preferably 20–40 weight percent, in emulsifiable concentrate; 10–70 weight percent, preferably 20–50 weight percent, in flowable.

A wettable powder, a water soluble powder or an emulsifiable concentrate thus produced may be diluted with water to a specified concentration and used as a liquid suspension or a liquid emulsion for treating soils or plant foliage. Further, a flowable may be directly used for soil or foliage treatment, otherwise, it may be diluted with water to a specified concentration and used as a liquid suspension for treating soils or plant foliage.

Non-limitinh examples of herbicidal composition are illustrated by the following tests:

EXAMPLE 5

Wettable powder

|  | parts by weight |
|---|---|
| Compound No. 1 | 50 |
| White carbon | 12 |
| Diatomaceous earth | 30 |
| Sodium alkylsulfate | 8 |

These are mixed homogeneously and reduced to fine particles to provide a wettable powder containing 50% of active ingredient. In use, it is diluted to a desired concentration with water, and is sprayed as suspension.

EXAMPLE 6

Water soluble powder

|  | parts by weight |
|---|---|
| Compound No. 6 | 90 |
| Dialkylsulfosuccinate | 10 |

These are mixed homogeneously and reduced to fine particles to provide a water soluble powder containing 90% of active ingredient.

EXAMPLE 7

Emulsifiable concentrate

|  | parts by weight |
| --- | --- |
| Compound No. 2 | 20 |
| Xylene | 40 |
| Dimethylformamide | 30 |
| Polyoxyethylene phenyl ether | 10 |

These are mixed and dissolved to provide an emulsifiable concentrate containing 20% of active ingredient. In use, it is diluted to a desired concentration with water, and sprayed as an emulsion.

EXAMPLE 8

Flowable

|  | parts by weight |
| --- | --- |
| Compound No. 6 | 30 |
| Sun spray-7N (commercial product of Sun Oil Co., Ltd.) | 60 |
| Polyoxyethylene alkylether | 5 |
| Sorbitan alkylate | 5 |

These are mixed homogeneously to provide a flowable containing 30% of active ingredient.

The herbicidal effects of compounds are illustracted by the following tests:

Test 1

Seeds of wild oat and corn were planted in each pot having a surface area of 100 cm² and kept in a green house. When the plants were grown to 2-3 leaves and 3 leaves stage respectively, aqueous suspensions, prepared by diluting an emulsifiable concentrate with water to specified concentration containing 400 ppm and 200 ppm of active ingredient were sprayed on the foliage of the test plants at a rate of 100 l/10 are, and the pots were kept in a green house. Twenty eight days after spraying, the degree of damage to each plant was observed and evaluated on the scale of value of 0–10, which has the following meanings:

| Degree of Damage | |
| --- | --- |
| 0 | 0% |
| 2 | 20-29% |
| 4 | 40-49% |
| 6 | 60-69% |
| 8 | 80-89% |
| 10 | 100% |

1, 3, 5, 7 and 9 mean the intermediate degree between 0 and 2, 2 and 4, 4 and 6, 6 and 8, and 8 and 10 respectively.

The results are shown in Table 2.

TABLE 2

| Compound No. | Application Rate (g/10 are) | Degree of Damage wild oat | corn |
| --- | --- | --- | --- |
| 1 | 40 | 10 | 2 |
|  | 20 | 10 | 1 |
| 2 | 40 | 10 | 2 |
|  | 20 | 10 | 1 |
| 3 | 40 | 10 | 1 |
|  | 20 | 10 | 0 |
| 4 | 40 | 10 | 1 |
|  | 20 | 10 | 0 |
| 5 | 40 | 10 | 1 |
|  | 20 | 10 | 0 |
| 6 | 40 | 10 | 1 |
|  | 20 | 10 | 0 |
| 7 | 40 | 10 | 1 |
|  | 20 | 10 | 0 |
| Comparative compound A | 40 | 9 | 10 |
|  | 20 | 7 | 7 |
| Comparative compound B | 40 | 10 | 10 |
|  | 20 | 8 | 7 |

Comparative Compound A: 2-[1-(ethoxyimino)propyl]-3-hydroxy-5-phenyl-2-cyclohexen-1-one
Comparative Compound B: 2-[1-(ethoxyimino)propyl]-3-hydroxy-5-(4-methoxyphenyl)-2-cyclohexen-1-one

What we claim is:

1. A compound having the formula

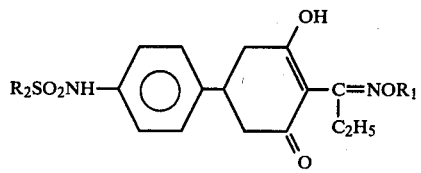

wherein
$R_1$ is ethyl or allyl; and
$R_2$ is alkyl having 1 to 4 carbon atoms;
and a metal salt of said compound selected from the group consisting of alkali metal salts and calcium salts.

* * * * *